(12) United States Patent
Kawagishi (10) Patent No.: US 10,861,606 B2
(45) Date of Patent: Dec. 8, 2020

(54) MEDICAL DIAGNOSIS SUPPORT APPARATUS AND MEDICAL DIAGNOSIS SUPPORT METHOD

(71) Applicant: CANON KABUSHIKI KAISHA, Tokyo (JP)

(72) Inventor: Masami Kawagishi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 281 days.

(21) Appl. No.: 15/916,361

(22) Filed: Mar. 9, 2018

(65) Prior Publication Data

US 2018/0204644 A1    Jul. 19, 2018

Related U.S. Application Data

(63) Continuation of application No. 13/423,495, filed on Mar. 19, 2012, now Pat. No. 9,940,438.

(30) Foreign Application Priority Data

Mar. 28, 2011    (JP) ................................. 2011-070397
Jan. 26, 2012    (JP) ................................. 2012-014584

(51) Int. Cl.
| | | |
|---|---|---|
| G16H 50/70 | (2018.01) | |
| G06F 19/00 | (2018.01) | |
| G16H 30/20 | (2018.01) | |
| G16H 50/20 | (2018.01) | |

(52) U.S. Cl.
CPC .......... *G16H 50/70* (2018.01); *G06F 19/321* (2013.01); *G16H 30/20* (2018.01); *G16H 50/20* (2018.01)

(58) Field of Classification Search
USPC .......................................................... 706/52
See application file for complete search history.

(56) References Cited

U.S. PATENT DOCUMENTS

| | | |
|---|---|---|
| 7,458,936 B2 | 12/2008 | Zhou et al. |
| 7,483,554 B2 | 1/2009 | Kotsianti et al. |
| 7,640,051 B2 | 12/2009 | Krishnan et al. |
| 8,880,455 B2 | 11/2014 | Kawagishi et al. |

(Continued)

FOREIGN PATENT DOCUMENTS

| | | |
|---|---|---|
| JP | 07-117972 | 12/1995 |
| JP | 3226400 | 11/2001 |

OTHER PUBLICATIONS

Ahmed et al., "Case studies on the Clinical Applications using Case-Based Reasoning", Proceeding of the Federated Conference on Computer Science and Information Systems (2012) 3-10.

(Continued)

*Primary Examiner* — Michael B Holmes
(74) *Attorney, Agent, or Firm* — Venable LLP (57) ABSTRACT

A medical diagnosis support apparatus which provides information for supporting medical diagnosis includes an inference unit which obtains an inference result based on a combination of already input information and each non-input information, an evaluation unit which evaluates each non-input information by using an inference result on the already input information which is obtained by the inference unit and an inference result on the each non-input information which is obtained by the inference unit, and a selection unit which selects non-input information to be presented from the non-input information based on the evaluation obtained by the evaluation unit.

11 Claims, 8 Drawing Sheets

(56) References Cited

U.S. PATENT DOCUMENTS

| | | | |
|---|---|---|---|
| 8,949,171 B2 | 2/2015 | Kawagishi | |
| 9,117,009 B2 * | 8/2015 | Iizuka | G16H 15/00 |
| 9,361,580 B2 * | 6/2016 | Kawagishi | G06N 5/02 |
| 9,384,326 B2 * | 7/2016 | Kawagishi | G06Q 50/22 |
| 9,436,915 B2 * | 9/2016 | Kawagishi | G06N 5/048 |
| 9,438,915 B1 * | 9/2016 | Bultje | H04N 19/60 |
| 9,519,866 B2 * | 12/2016 | Kawagishi | G16H 50/70 |
| 9,715,657 B2 * | 7/2017 | Kawagishi | G06N 5/04 |
| 9,734,299 B2 * | 8/2017 | Yakami | G16H 50/20 |
| 9,734,300 B2 * | 8/2017 | Kawagishi | A61B 6/461 |
| 9,916,425 B2 * | 3/2018 | Kawagishi | G16H 30/20 |
| 9,940,438 B2 * | 4/2018 | Kawagishi | G16H 50/70 |
| 9,940,715 B2 * | 4/2018 | Fujimoto | G16H 30/40 |
| 10,282,671 B2 * | 5/2019 | Kawagishi | G16H 15/00 |
| 10,290,096 B2 * | 5/2019 | Kawagishi | G16H 50/20 |
| 10,726,344 B2 * | 7/2020 | Kawagishi | A61B 6/461 |
| 2004/0193036 A1 | 9/2004 | Zhou et al. | |
| 2006/0200010 A1 | 9/2006 | Rosales et al. | |
| 2009/0080732 A1 | 3/2009 | Zhou et al. | |
| 2011/0093243 A1 | 4/2011 | Tawhai et al. | |
| 2011/0199390 A1 | 8/2011 | Iizuka et al. | |
| 2011/0213748 A1 | 9/2011 | Kawagishi et al. | |
| 2012/0136882 A1 | 5/2012 | Kawagishi et al. | |
| 2012/0176408 A1 | 7/2012 | Moriya | |

OTHER PUBLICATIONS

Doi, "Current status and future potential of computer-aided diagnosis in medical imaging", British Journal of Radiology, vol. 78 (2005) S3-19.

Duin et al., "Structural Inference of Sensor-Based Measurements", SSPR&SPR 2006, LNCS 4109 (2006) 41-55.

Hoffrage et al., "How to Improve the Diagnostic Inferences of Medical Experts", Experts in Science and Society (2004) 249-68.

Lemmer et al., "Efficient Minimum Information Updating for Bayesian Inferencing in Expert Systems", AAAI-82 Proceedings (1982) 424-27.

Lucas, "Certainty-factor-like structures in Bayesian belief networks", Knowledge-Based Systems, vol. 14 (2001) 327-35.

Madsen et al., "The Hugin Tool for Probabilistic Graphical Models", International Journal on Artificial Intelligence Tools, vol. 14, No. 3 (2005) 507-43.

Röbesaat et al., "Analysis of LVAD Log Files for the Early Detection of Pump Thrombosis", IEEE Symposium on Computers and Communications (2017) 236-41.

Szolovits, "Uncertainty and Decisions in Medical Informatics", Methods of Information in Medicine, vol. 34 (1995) 111-21.

Tenenbaum et al., "Theory-based Bayesian models of inductive learning and reasoning", TRENDS in Cognitive Sciences, vol. 10, No. 7 (2006) 309-18.

Wang et al., "Using Sensitivity Analysis for Selective Parameter Update in Bayesian Network Learning", AAAI Technical Report SS-02-03, Compilation (2002) 1-8.

Zhu et al., "Application of Evidential Reasoning Rules to Identification of Asthma Control Steps in Children", Cong Xu 2016 22nd International Conference on Automation and Computing (2016) 444-49.

\* cited by examiner

| m | $E_{vm}$ (FINDING-STATE NAME) | $P_c(E_{vm})$ | $IR(E_{vm})$ | $W(E_{vm})(\times 10^{-2})$ |
|---|---|---|---|---|
| 1 | {$S_{21}$(LOBATION-STRONG)} | 0.143 | (−)0.274 | (−)3.92 |
| 2 | {$S_{22}$(LOBATION-INTERMEDIATE)} | 0.202 | (−)0.168 | (−)3.39 |
| 3 | {$S_{23}$(LOBATION-WEAK)} | 0.254 | (+)0.135 | (+)3.43 |
| 4 | {$S_{24}$(LOBATION-NONE)} | 0.401 | (+)0.178 | (+)7.14 |
| 5 | {$S_{61}$(CALCIFICATION-PRESENT)} | 0.398 | (−)0.113 | (−)4.50 |
| 6 | {$S_{62}$(CALCIFICATION-ABSENT)} | 0.602 | (+)0.075 | (+)4.52 |
| 7 | {$S_{81}$(ENGULFMENT (PLEURA)-PRESENT)} | 0.303 | (−)0.107 | (−)3.24 |
| 8 | {$S_{82}$(ENGULFMENT (PLEURA)-SUSPICIOUS)} | 0.405 | (+)0.085 | (+)3.44 |
| 9 | {$S_{83}$(ENGULFMENT (PLEURA)-ABSENT)} | 0.292 | (+)0.212 | (+)6.19 |

FIG. 8

MEDICAL DIAGNOSIS SUPPORT APPARATUS AND MEDICAL DIAGNOSIS SUPPORT METHOD

BACKGROUND OF THE INVENTION

Field of the Invention

The present invention relates to a medical diagnosis support apparatus and a medical diagnosis support method.

Description of the Related Art

In the medical field, a doctor displays the medical images obtained by imaging a patient on a monitor, interprets the displayed medical images, and observes the state of a morbid portion and temporal changes in it. Apparatuses which generate this type of medical images include, for example, an X-ray CT (Computed Tomography) apparatus, MRI (Magnetic Resonance Imaging) apparatus, and ultrasonic apparatus. Each diagnosis (imaging diagnosis) using these medical images can be divided into the step of finding an abnormal shade or the like from the medical images and obtaining the characteristics of the shade and the step of performing differential diagnosis to identify the shade.

Conventionally, there has been developed a medical diagnosis support apparatus which infers the identification of an abnormal shade by using the characteristics (interpretation findings) of the shade as input information and presents the resultant information for the purpose of supporting differential diagnosis by doctors. For example, there has been proposed an apparatus which calculates the probability of a given shade in a chest X-ray CT image being a malignant tumor and the probability of the shade being a benign tumor and presents the resultant information. In general, the following is a proper procedure when using such an apparatus in an actual clinical site. First of all, the doctor performs differential diagnosis. The doctor then refers to the inference result output from the medical diagnosis support apparatus as reference information.

A problem in this case is that if there are many pieces of information which have not been input, the accuracy of inference by the apparatus is low. Attempts have therefore been made to obtain more reliable inference results by making an apparatus select non-input information necessary for inference and prompt the doctor to add the information.

For example, Japanese Patent No. 3226400 has disclosed a technique of selecting and presenting non-input information to be noted from the inference result (current inference result) obtained by an apparatus based on information which has already been input (already input information) and the inference result obtained when non-input information is added to already input information. This technique is designed to calculate the influence degree of each non-input information with respect to a current inference result and present non-input information exhibiting a high influence degree. This makes it possible to present non-input information which greatly influences the inference result obtained by the apparatus based on already input information.

In addition, Japanese Patent Publication No. 7-117972 discloses a technique of presenting hypothetical information by using a current inference result. This technique uses a knowledge database to present hypothetical symptoms inferred from the current inference result. This makes it possible to present non-input information exhibiting strong relevance to the current inference result.

According to Japanese Patent No. 3226400, however, non-input information to be noted has been selected based on only criterion whether it has great influence on the inference result obtained by the apparatus based on already input information. For this reason, this technique may present information (finding) which is not likely to exist as non-input information to be noted.

On the other hand, the technique disclosed in Japanese Patent Publication No. 7-117972 presents only non-input information exhibiting strong relevance to a current inference result, and gives no consideration of relevance to already input information. For this reason, this technique presents information exhibiting weak relevance to already input information or does not present information which exhibits strong relevance to already input information but gives contradiction to a current inference result.

SUMMARY OF THE INVENTION

One embodiment is configured to select and present non-input information, of non-input information existing with high possibility, which should be preferentially checked by a doctor.

According to one embodiment of the present invention, there is provided a medical diagnosis support apparatus which provides information for supporting medical diagnosis, comprising: an inference unit configured to obtain an inference result based on a combination of already input information and each non-input information; an evaluation unit configured to evaluate each non-input information by using an inference result on the already input information which is obtained by the inference unit and an inference result on the each non-input information which is obtained by the inference unit; and a selection unit configured to select non-input information to be presented from the non-input information based on the evaluation obtained by the evaluation unit.

According to another embodiment of the present invention, there is provided a medical diagnosis support method which provides information for supporting medical diagnosis, comprising: an inference step of obtaining an inference result based on a combination of already input information and each non-input information; an evaluation step of evaluating each non-input information by using the inference result on the already input information and the inference result on the each non-input information; and a selection step of selecting non-input information to be presented from the non-input information based on the evaluation.

In this manner, it is possible to select and present non-input information, of non-input information existing with high possibility, which should be preferentially checked by a doctor.

Further features of the present invention will become apparent from the following description of exemplary embodiments (with reference to the attached drawings).

DESCRIPTION OF THE EMBODIMENTS

A medical diagnosis support apparatus and medical diagnosis support method according to an embodiment will be described below with reference to the accompanying drawings.

First Embodiment

A medical diagnosis support apparatus according to the first embodiment obtains medical information associated with a case as a target (target case) as already input information, and performs diagnosis support associated with the target case. Note that the following is a case in which the apparatus supports imaging diagnosis on an abnormal shade in the lung. The medical diagnosis support apparatus obtains at least an interpretation finding associated with an abnormal shade in the lung as already input information, performs inference about the type of abnormality (diagnosis name) of the abnormal shade, and presents diagnosis support information based on the inference result. Note that a region as an inference target is not limited to the lung, and other regions can be set as targets. In addition, an inference target is not limited to the type of abnormality, and inference about benignity/malignity can be an inference target. The diagnosis names, interpretation findings which can be input, and the like are merely examples to explain the steps in the processing performed by the medical diagnosis support apparatus.

Figure 1:
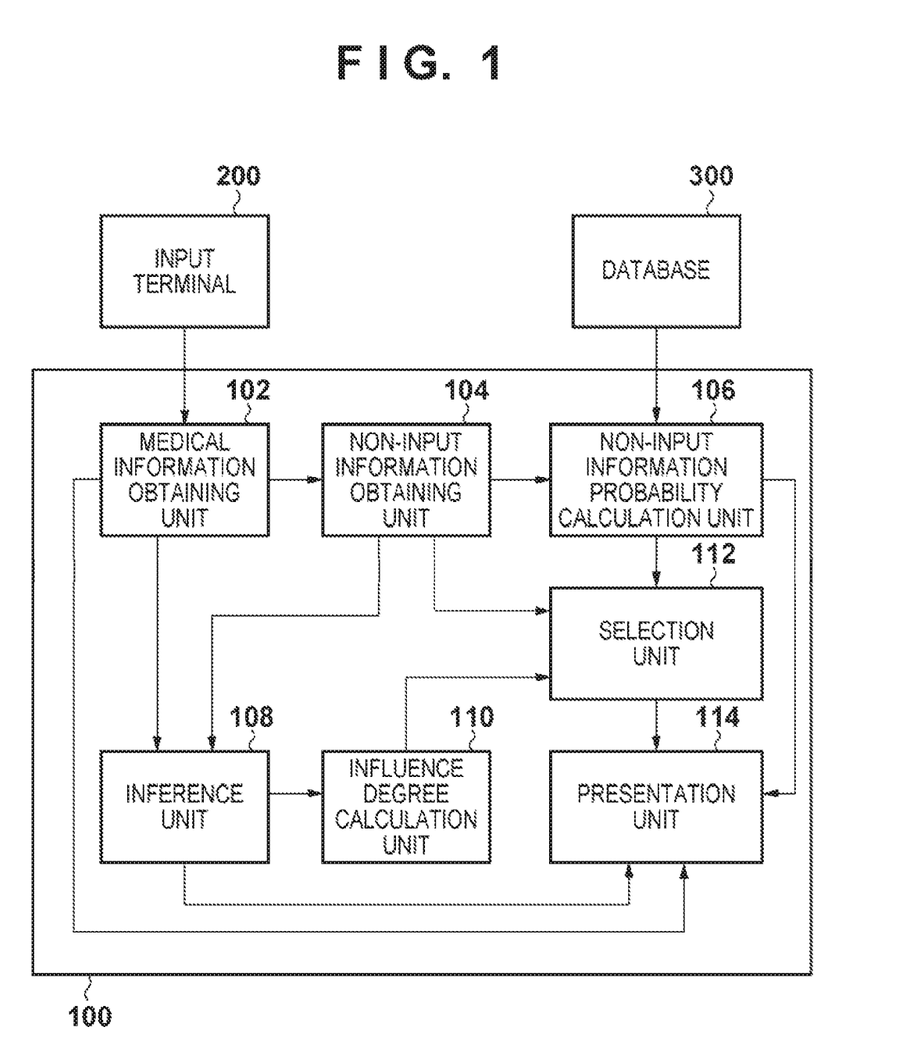
FIG. 1 is a block diagram showing the functional arrangement of a medical diagnosis support apparatus according to the first embodiment.

FIG. 1 shows the arrangement of a medical diagnosis support apparatus according to the first embodiment. A medical diagnosis support apparatus 100 according to this embodiment is connected to an input terminal 200 and a database 300, as shown in FIG. 1.

The terminal 200 can obtain the data of a target case associated with an abnormal shade in the lung (for example, the information of medical images and electronic medical records) from a server (not shown). Alternatively, external storage devices such as an FDD, HDD, CD drive, DVD drive, MO drive, and ZIP drive may be connected to the apparatus to obtain the data of a target case from these drives. The apparatus then displays, on a display device, the data of the target case input via the input terminal 200 in a form that allows a user (doctor) to interpret. The user (doctor) interprets the data of the target case displayed on the display device, and inputs the interpretation result as interpretation findings with the input terminal 200. The input terminal 200 obtains the interpretation findings input by the user (doctor) as already input information (medical information which has already been input). In this embodiment, the user (doctor) inputs interpretation findings on the medical image displayed on the display device by using a mouse and a keyboard. Note that this processing is implemented by making the input terminal 200 have a function of allowing the user to select information with a GUI by using, for example, interpretation finding input support method based on a template form. The input terminal 200 transmits the interpretation findings (already input information) about the abnormal shade in the lung as a target case and accompanying data (representative images and the like) to the medical diagnosis support apparatus 100 via a network such as a LAN in accordance with a request from the user (doctor).

The database 300 stores already input information input in the past for each region as a diagnosis target. The database 300 stores, for example, already input information of a past case associated with an abnormal shade in the lung. Using the database 300 can obtain the total number of pieces of already input information stored, all the medical information items which can be input with respect to a region as a diagnosis target, the occurrence frequencies of the items, the co-occurrence frequencies between the items, and the like. The information held in the database 300 is transmitted to the medical diagnosis support apparatus 100 via a network such as a LAN.

The medical diagnosis support apparatus 100 includes constituent elements described below. A medical information obtaining unit 102 obtains medical information (already input information) about a region as a medical diagnosis target, which has been input from the input terminal 200 to the medical diagnosis support apparatus 100, and accompanying data (a representative image and the like). For example, in a case in which a region as a medical diagnosis target is the lung, a medical information obtaining unit 102 obtains interpretation findings (already input information) about an abnormal shade in the lung as the target case and accompanying data. The a medical information obtaining unit 102 outputs already input information to a non-input information obtaining unit 104, an inference unit 108, and a presentation unit 114. In addition, the medical information obtaining unit 102 outputs the obtained medical information and accompanying data (a representative image and the like) to the presentation unit 114.

The non-input information obtaining unit 104 can obtain all the items of medical information (interpretation findings) which can be input with respect to a target region (for example, the lung) for medical diagnosis by referring to the database 300. The non-input information obtaining unit 104 obtains, as non-input information, at least one piece of information obtained by subtracting already input information from all the items of medical information which can be input and are obtained from the database 300. The non-input information obtaining unit 104 outputs the obtained non-input information to a non-input information probability calculation unit 106, the inference unit 108, and the presentation unit 114.

The non-input information probability calculation unit 106 calculates the probability (occurrence probability) of the event represented by each non-input information existing in a region as a medical diagnosis target based on the relationship between already input information and the non-input information. The non-input information probability calculation unit 106 calculates the occurrence probability of each non-input information concerning information about items which can be input which are held by the database 300. A method of calculating an occurrence probability will be described later. The non-input information probability calculation unit 106 outputs the calculated occurrence probability to a selection unit 112 and the presentation unit 114. The inference unit 108 infers an abnormality (abnormality candidate) in a region as a medical diagnosis target by using a predetermined inference technique based on the already input information of an abnormal shade in the lung obtained by the medical information obtaining unit 102. For example, the inference unit 108 infers the diagnosis name of an abnormal shade in the lung as an already input information inference result. The inference unit 108 infers the diagnosis name of the abnormal shade of the lung (non-input information inference result) as an abnormality (abnormality candidate) in the region as the medical diagnosis target by using a combination of the already input information and each non-input information obtained by the non-input information obtaining unit 104. The inference unit 108 outputs the already input information inference result and non-input information inference result as inference results to an influence degree calculation unit 110 and the presentation unit 114.

The influence degree calculation unit 110 calculates the influence degree of each non-input information (non-input information influence degree) with respect to inference by using the already input information inference result obtained by the inference unit 108 and each non-input information inference result. In this case, an influence degree (non-input information influence degree) is a value indicating the degree to which each non-input information should be preferentially checked by the doctor. The influence degree calculation unit 110 calculates the influence degree of each non-input information. For example, the influence degree calculation unit 110 calculates an influence degree b1 with respect to non-input information a1, and an influence degree b2 with respect to non-input information a2. If the influence degree b1 (first influence degree) is higher than the influence degree b2 (second influence degree), it is possible to determine that the non-input information a1 is higher in influence on the inference than the non-input information a2. The influence degree calculation unit 110 outputs the calculated influence degree (non-input information influence degree) to the selection unit 112.

The selection unit 112 selects presentation non-input information from non-input information based on the occurrence probability of each non-input information calculated by the non-input information probability calculation unit 106 and the influence degree of each non-input information obtained by the influence degree calculation unit 110. The selection unit 112 then outputs the selected presentation non-input information to the presentation unit 114. The presentation unit 114 presents (displays) the presentation non-input information selected by the selection unit 112 to the display device. This makes it possible to efficiently present non-input information to be preferentially checked by the doctor.

At least some of the functional arrangements of the respective units of the medical diagnosis support apparatus 100 shown in FIG. 1 may be implemented as independent devices. In addition, the functional arrangement of each unit of the medical diagnosis support apparatus 100 may be implemented by software.

Figure 2:
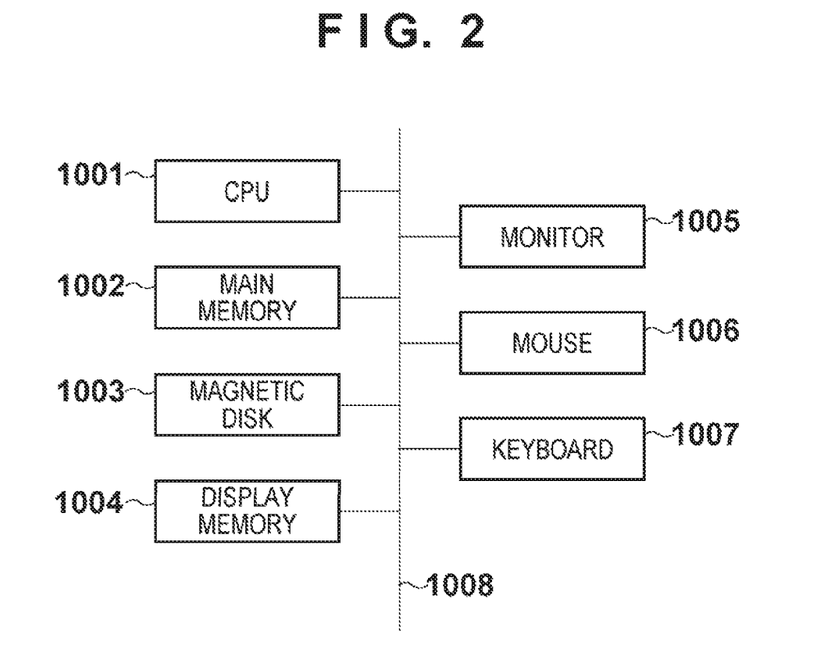
FIG. 2 is a block diagram showing the basic arrangement of a computer which implements each unit of the medical diagnosis support apparatus by software.

FIG. 2 shows the basic arrangement of a computer for implementing the function of each unit shown in FIG. 1 by executing software. A CPU 1001 controls the operation of each constituent element. A main memory 1002 stores control programs executed by the CPU 1001, and provides a work area at the time of execution of a program by the CPU 1001. A magnetic disk 1003 stores an operating system (OS), device drives for peripheral devices, and various types of application software including programs for the execution of processing (to be described later). A display memory 1004 temporarily stores the display data generated by the presentation unit 114. A monitor 1005 is, for example, a CRT monitor or liquid crystal monitor, and displays images, texts, and the like based on data from the display memory 1004. The monitor 1005 (display device) also displays the result processed by the presentation unit 114. A mouse 1006 and a keyboard 1007 are respectively used by the user to perform input operations such as pointing input operation and inputting of characters and the like. The respective constituent elements are communicatively connected to each other via a common bus 1008.

Figure 3:
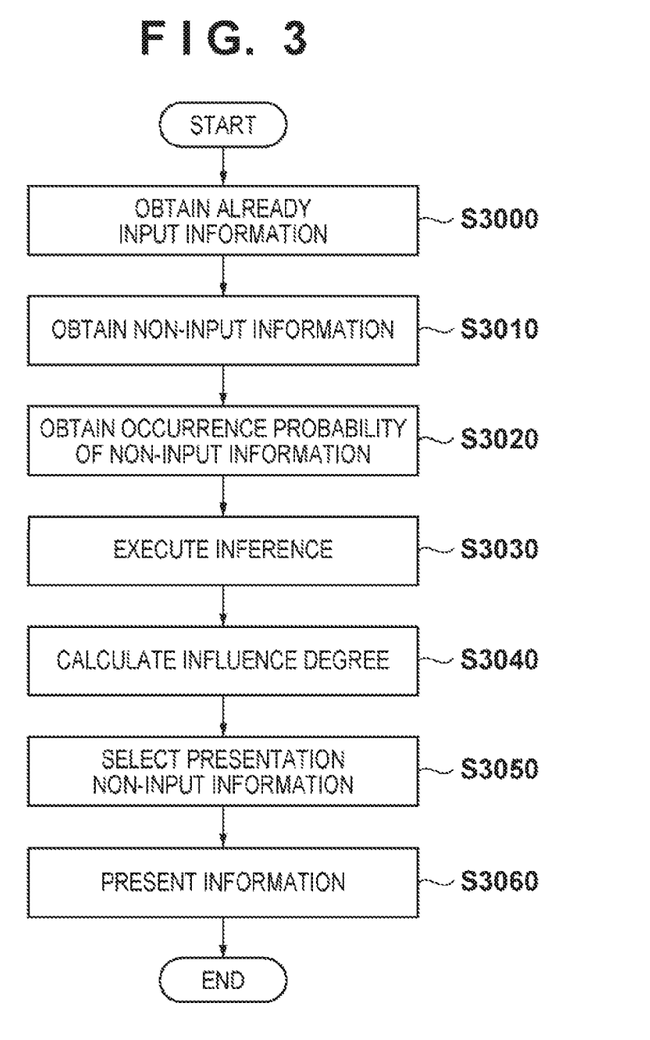
FIG. 3 is a flowchart showing a processing procedure for a medical diagnosis support method according to the first embodiment.

Overall processing performed by the medical diagnosis support apparatus 100 will be described next with reference to the flowchart of FIG. 3. This embodiment is implemented by causing the CPU 1001 to execute a program which is stored in the main memory 1002 and implements the function of each unit.

Assume that in the following description, each interpretation finding is represented by Ij (j=1 to n), and this apparatus handles n types of interpretation findings I1 to In. For example, "Shape" of I1 represents the shape of an abnormal shade, and "Lobation" of I2 represents the degree of lobation in an abnormal shade. In addition, "Engulfment (Blood Vessel)" of In represents the presence/absence of the engulfment of a blood vessel in an abnormal shade.

In the following description, a state (discrete value) which Ij can take is written as Sjk. The range of k takes various values depending on Ij. For example, in "Shape" of the interpretation finding I1, k is 3, which takes three states, namely S11 "spherical", S12 "lobulated", and S13 "irregular". In the following description, a set of Ij is written as N, and a set of Sjk is written as E. Assume however that a plurality of states (discrete values) Sjk which Ij can take do not simultaneously exist in one E. For example, if I1 takes S11, S12, and S13, and I2 takes S21, S22, S23, and S24, E={S11, S21} indicates the states of "Shape" and "Lobation", and can take both the states. However, E={S11, S12} indicates the two different states ("spherical" and "lobulated") of one interpretation finding, and cannot take both the states. This is because one interpretation finding item takes only one state.

In this case, a set of interpretation finding items corresponding to already input information is written as Nf, and a set of states of Nf is written as Ef. The set Ef corresponds to already input information. A set of interpretation findings other than already input information is written as Nf', and a set including states of Nf' as elements is written as Evm (m=1, 2, ... ). In this case, Evm corresponds to non-input information. In addition, the occurrence probability of the non-input information Evm and the influence degree of the non-input information Evm are respectively written as Pc(Evm) and IR(Evm).

In addition, a diagnosis name is written by using the symbol "D". In this embodiment, diagnosis names take three values, namely primary lung cancer, lung cancer metastasis, and others, respectively written as D1, D2, and D3. In addition, the inference probability of a diagnosis name Dr (r=1, 2, 3) when E is input is written as P(Dr|E).

In step S3000, the medical information obtaining unit 102 of the medical diagnosis support apparatus 100 obtains already input information about an abnormal shade in the lung input to the medical diagnosis support apparatus 100 and accompanying data. Assume that the interpretation finding information obtained by the medical diagnosis support apparatus 100 in step S3000 is I1 "Shape": "spherical", I3 "Radial": "weak", ..., In "Engulfment (Blood Vessel)": "none". In this case, the set Nf of interpretation findings of the already input information is given as Nf={I1, I3, ..., In}, and the set Ef of the states of Nf is given as Ef={S11, S33, ..., Sn3}.

TABLE 1

| j | Ij (Item Name) | jk | Sjk (State Name) |
|---|---|---|---|
| 1 | Shape | 11 | spherical |
|   |   | 12 | lobulated |
|   |   | 13 | irregular |
| 2 | Lobation | 21 | strong |
|   |   | 22 | intermediate |
|   |   | 23 | weak |
|   |   | 24 | none |
| 3 | Radial | 31 | strong |
|   |   | 32 | intermediate |
|   |   | 33 | weak |
|   |   | 34 | none |
| ... |   |   |   |
| n | Engulfment (Blood Vessel) | n1 | present |
|   |   | n2 | suspicious |
|   |   | n3 | absent |

In step S3010, the non-input information obtaining unit 104 of the medical diagnosis support apparatus 100 obtains, as non-input information, at least one set based on information obtained by excluding the already input information from all the pieces of information which can be input. Consider, for example, a case in which Nf'={I2, I6, I8}, I2 takes S21, S22, S23, and S24, I6 takes S61 and S62, and I8 takes S81, S82, and S83. If, for example, the number of elements to be included in Evm is limited to one, the non-input information obtaining unit 104 obtains 4+2+3=9 pieces of non-input information. Alternatively, if the number of elements to be included is limited to two, the non-input information obtaining unit 104 obtains 4×2+4×3+2×3=26 pieces of non-input information.

In step S3020, the non-input information probability calculation unit 106 of the medical diagnosis support apparatus 100 obtains the occurrence probability of each non-input information based on the relationship between the already input information and the non-input information with respect to information which is held in the database 300 and associated with items which can be input. The non-input information probability calculation unit 106 outputs the obtained occurrence probabilities to the selection unit 112. This embodiment uses co-occurrence with already input information as an occurrence probability. Let $F(E_f \cup E_{vm})$ be the frequency (co-occurrence frequency) of a case including both a set (Ef) of already input information and a set (Evm) of non-input information, and ALL be the total number of cases stored in the database 300. In this case, an occurrence probability $P_c(E_{vm})$ of the non-input information is defined by the following equation using the total number of cases and the co-occurrence frequency.

$$P_C(E_{vm}) = \frac{F(E_f \cup E_{vm}) + 1}{ALL + 1} \quad (1)$$

As indicated by equation (1), the occurrence probability in this embodiment increases with an increase in co-occurrence frequency. In addition, $F(E_f \cup E_{vm})+1$ is set to make adjustment so as not to set the probability to 0. Note that it is possible to obtain the co-occurrence frequency $F(E_f \cup E_{vm})$ from the database 300 by a general method of creating a query to count the number of cases meeting the condition of having both Ef and Evm and executing the query to the database 300.

In step S3030, the inference unit 108 of the medical diagnosis support apparatus 100 infers the diagnosis name (already input information inference result) of the abnormal shade in the lung based on the already input information of the abnormal shade in the lung obtained in step S3000. In addition, the inference unit 108 infers the diagnosis name (non-input information inference result) of the abnormal shade in the lung by pairing the already input information and each non-input information calculated in step S3020. The inference unit 108 outputs the obtained already input information inference result and each non-input information inference result to the influence degree calculation unit 110.

As an inference technique at this time, it is possible to use one of various existing inference techniques such as a Bayesian network, neural network, and support vector machine. This embodiment uses a Bayesian network as an inference technique. The Bayesian network is an inference model using conditional probabilities. It is possible to obtain the inference probability of each diagnosis name when already input information is input (the probability of the case being each diagnosis name; also called a posterior probability). In this embodiment, the inference unit 108 obtains the probabilities of types D1, D2, and D3 of abnormal shades.

In step S3040, the influence degree calculation unit 110 of the medical diagnosis support apparatus 100 calculates the influence degree of each non-input information (non-input information influence degree) on inference by using the inference result on the non-input information. More specifically, the influence degree calculation unit 110 uses the occurrence probability of each non-input information calculated in step S3020 and the already input information inference result and each non-input information inference result obtained in step S3030. The influence degree calculation unit 110 outputs the obtained non-input information influence degrees to the selection unit 112.

In this embodiment, the non-input information influence degree IR(Evm) of the non-input information Evm is defined by the following equation. Note that Dmax is Dr which maximizes an inference probability P(Dr|Ef).

$$IR(E_{vm}) = |P(D_{max}|E_f \cup E_{vm}) - P(D_{max}|E_f)| \quad (2)$$

As indicated by equation (2), considering a diagnosis name exhibiting the highest inference probability when already input information is input, an influence degree in this embodiment indicates the degree of variation in inference probability of each diagnosis name upon addition of non-input information.

In step S3050, the selection unit 112 of the medical diagnosis support apparatus 100 selects presentation non-input information based on the occurrence probability of each non-input information obtained in step S3020 and the influence degree of each non-input information obtained in step S3040. More specifically, the selection unit 112 obtains an evaluation value W(Evm) of each non-input information Evm according to the following equation, and selects Evm which gives the maximum value W(Evm) as presentation non-input information.

$$W(E_{vm}) = P_c(E_{vm}) \cdot IR(E_{vm}) \quad (3)$$

Figure 6:
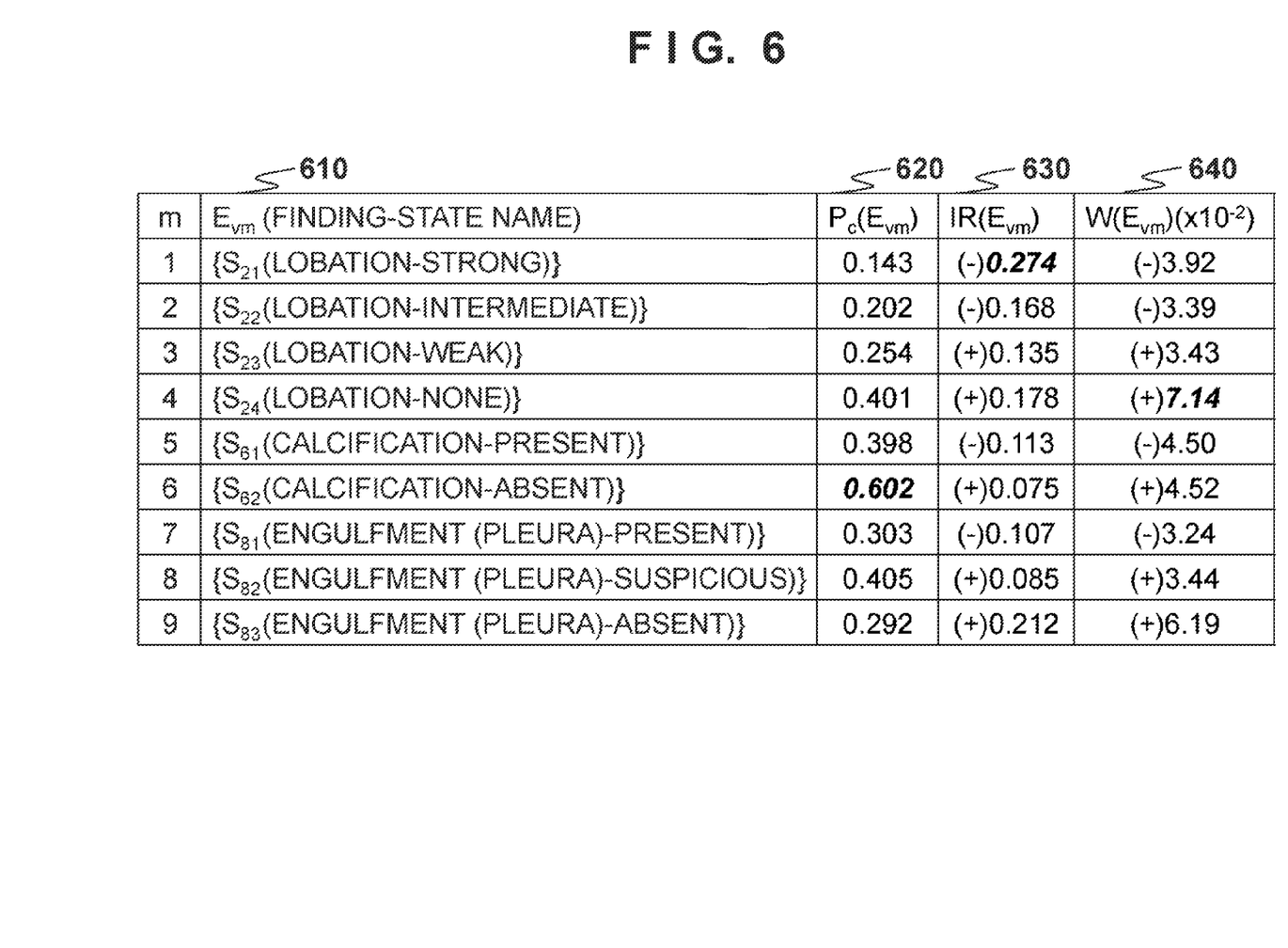
FIG. 6 is a view showing an example of the occurrence probability, influence degree, and evaluation value of each non-input information.

As indicated by equation (3), this embodiment uses the product of the occurrence probability and influence degree of non-input information as a selection criterion for presentation non-input information. FIG. 6 shows an example of the occurrence probability Pc(Evm) of each non-input information Evm, the influence degree IR(Evm) of the non-input information, and the evaluation value W(Evm) of the non-input information. As shown in FIG. 6, the maximum value of the occurrence probability Pc(Evm) is 0.602, which corresponds to {S62: calcification—none} of Ev6. The maximum value of the influence degree IR(Evm) is 0.274, which corresponds to {S21: lobation—strong} of Ev1. However, the maximum value of the influence degree IR(Evm) in consideration of Pc(Evm) and IR(Evm) is $7.14 \times 10^{-2}$, which corresponds to {S24: lobation—none] of Ev4. The selection unit 112 therefore selects {S24: lobation—none] of Ev4 as presentation input information.

In step S3060, the presentation unit 114 displays, on the monitor 1005, the information (already input information and a representative image) about the abnormal shade in the lung obtained in step S3000 and the already input information inference result obtained in step S3030. The presentation unit 114 also displays the presentation non-input information obtained in step S3050 on the monitor 1005. Furthermore, the presentation unit 114 displays, on the monitor 1005, the occurrence probability of the non-input information calculated in step S3020 and the non-input information inference result on the non-input information obtained in step S3030.

Figure 4:
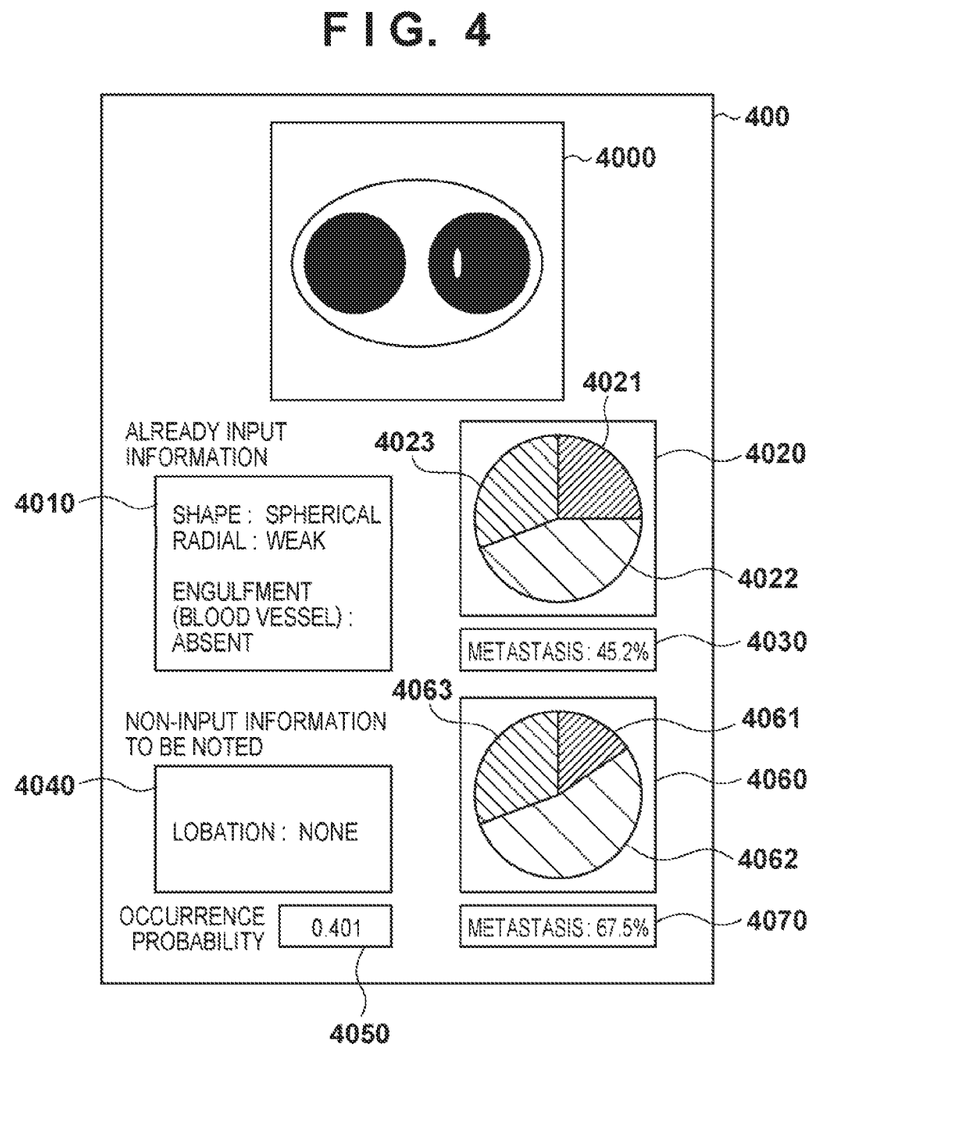
FIG. 4 is a view showing an example of presented information in the first embodiment.

FIG. 4 shows an example of presented information displayed on the monitor 1005 by the presentation unit 114. Presented information 400 includes a representative image 4000 of the abnormal shade in the lung, already input information 4010 of the abnormal shade in the lung obtained in step S3000, and an already input information inference result 4020 inferred in step S3030. The monitor 1005 displays in a pie chart, as the already input information inference result 4020, an inference probability 4021 of a primary lung cancer in the already input information inference result, an inference probability 4022 of a lung cancer metastasis in the already input information inference result, and inference probability 4023 of others in the already input information inference result. In addition, the presented information 400 includes a diagnosis name exhibiting the highest inference probability among the respective diagnosis names and a probability 4030 of the diagnosis name The presented information 400 also includes presentation non-input information 4040 obtained in step S3050, an occurrence probability 4050 of the non-input information calculated in step S3020, and a non-input information inference result 4060 inferred in step S3030. The monitor 1005 displays, as the non-input information inference result 4060 in a pie chart, an inference probability 4061 of a primary lung cancer in the non-input information inference result, an inference probability 4062 of the lung cancer metastasis in the non-input information inference result, and an inference probability 4063 of others in the non-input information inference result. The presented information 400 also includes a diagnosis name exhibiting the highest inference probability among the respective diagnosis manes and a probability 4070 of the diagnosis name.

The user (doctor) can check non-input information which should be preferentially seen and its influence by referring to an already input information inference result on already input information as an input and a non-input information inference result on non-input information exhibiting the highest influence as an input. When the user (doctor) performs diagnosis, referring to the result presented by the medical diagnosis support apparatus will provide some help in the diagnosis.

The medical diagnosis support apparatus according to this embodiment calculates the occurrence probability of at least one piece of non-input information, performs inference with respect to already input information and a combination of already input information and each non-input information, and presents information based on each occurrence probability and the influence degree using the inference result. This makes it possible to check information to be preferentially seen in consideration of the probability of an event represented by non-input information existing in an image of a region obtained as already input information, instead of simple variations in inference result. In addition, since the influence degree of non-input information is calculated by the method which does not depend only on an already input information inference result, it is possible to provide a mechanism of presenting even information negating an already input information inference result as information to be preferentially checked.

Second Embodiment

The first embodiment obtains the occurrence probability of non-input information by using the co-occurrence frequency between already input information and the non-input information. However, the method of obtaining occurrence probabilities is not limited to this, and other methods may be used. A medical diagnosis support apparatus according to the second embodiment includes the second inference unit which infers the occurrence probability of non-input information.

Figure 7:
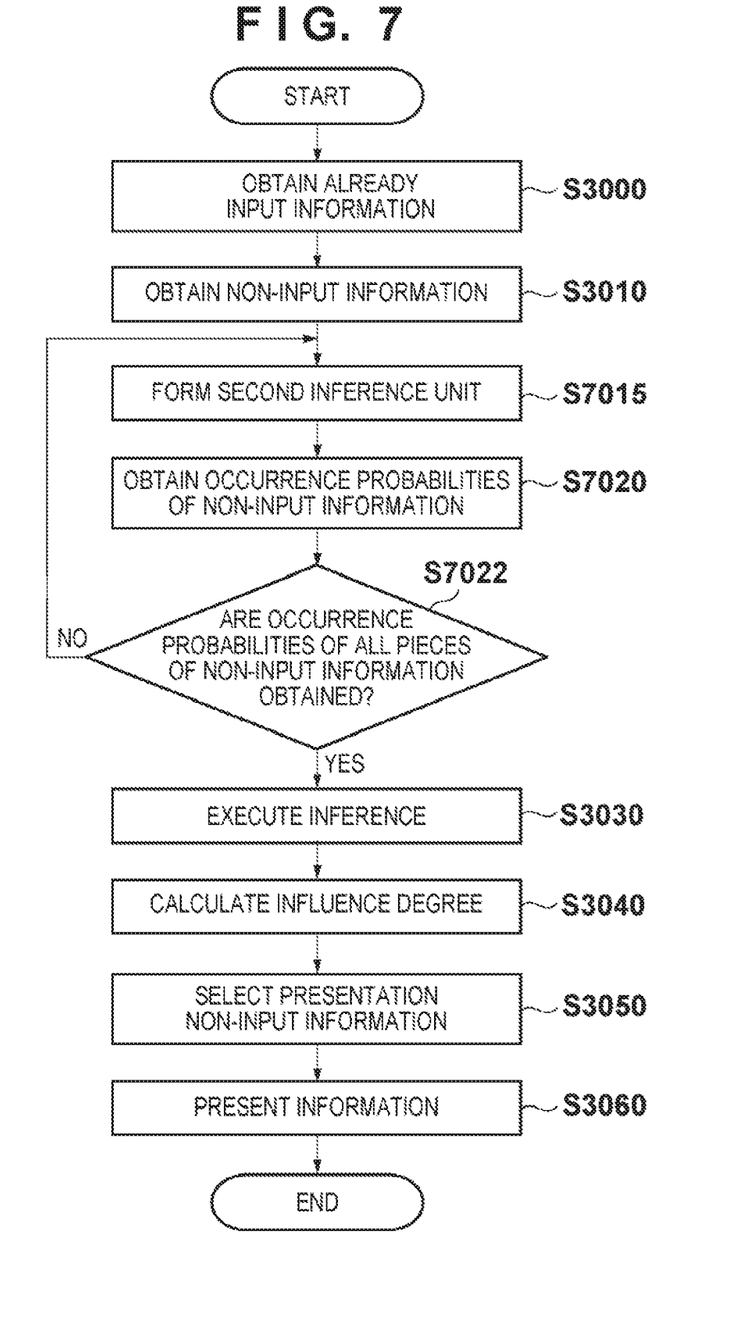
FIG. 7 is a flowchart showing a processing procedure for a medical diagnosis support method according to one embodiment.

Note that the arrangement of the medical diagnosis support apparatus according to this embodiment is the same as that shown in FIG. 1 in the first embodiment. However, the second embodiment differs from the first embodiment in that a non-input information probability calculation unit 106 includes the second inference unit which receives already input information and outputs non-input information, and calculates an occurrence probability by using the second inference unit. The medical diagnosis support apparatus according to this embodiment will be described below with reference to only portions different from the first embodiment. The basic arrangement of a computer which implements a medical diagnosis support apparatus 100 by executing software is the same as that shown in FIG. 2 in the first embodiment. FIG. 7 is a flowchart for explaining overall processing performed by the medical diagnosis support apparatus 100.

The processing in steps S3000 and S3010 is the same as that in the first embodiment.

In step S7015, the medical diagnosis support apparatus 100 forms the second inference unit as the processing performed by the non-input information probability calculation unit 106. In this embodiment, processing in step S7015 is executed as follows. First of all, the non-input information probability calculation unit 106 obtains a set Nv of interpretation findings of elements (states) included in non-input information Evm. Subsequently, the non-input information probability calculation unit 106 obtains all cases including all the interpretation findings of the set Nv as already input information from a database 300 by a general method. The medical diagnosis support apparatus 100 then forms the second inference unit which infers the occurrence probabilities of the states of Nv (that is, Evm) from information Nv' which can be input, from which Nv is excluded. Assume that the apparatus obtains Ef={S11, S33, . . . , Sn3] and Nf'={I2, I6, I8} in step S3010. Assume that in this case, I2 takes S21, S22, S23, and S24, I6 takes S61 and S62, I8 takes S81, S82, and S83, and the number of elements included in Evm is limited to one. When Evm={S21}, Nv={I2}, and the medical diagnosis support apparatus 100 obtains all the cases included in I2 from the database 300. That is, unlike the first embodiment, the second embodiment obtains cases without considering already input information. The apparatus then forms the second inference unit which infers the occurrence probabilities of interpretation findings other than I2, that is, the states (S21, S22, S23, and S24) of I2 from I1 to In (except for I2), based on the obtained cases. It is possible to use one of various existing inference techniques as the second inference technique like the inference technique in the first embodiment. This embodiment uses a Bayesian network as the second inference technique.

In step S7020, the medical diagnosis support apparatus 100 obtains the occurrence probability of each non-input information Evm using the second inference unit formed in step S7015 as processing (occurrence probability obtaining processing) performed by the non-input information probability calculation unit 106. More specifically, the apparatus inputs the already input information Ef to the second inference unit and calculates the occurrence probability of the non-input information Evm, thereby obtaining the occurrence probability. The apparatus outputs the obtained occurrence probability to a non-input information obtaining unit 104. In step S7022, the medical diagnosis support apparatus 100 determines whether the occurrence probabilities of all the pieces of non-input information Evm have been obtained. If all the occurrence probabilities have been obtained, the process advances to step S3030. If all the occurrence probabilities have not been obtained, the process returns to step S7015 to form the second inference unit for new non-input information EVm. In the above case, since the apparatus obtains nine pieces of information Evm, the apparatus repeats the processing in steps S7015 to S7022 nine times. Obviously, this is an example, and embodiments of the present invention are not limited to this. For example, the apparatus may form the second inference unit which simultaneously obtains the occurrence probabilities of S21, S22, S23, and S24 in step S7015. In this case, the apparatus forms the second inference unit by the number of times corresponding to the number of elements of Nf, and obtains the occurrence probabilities of the pieces of non-input information Evm. In the above case, to obtain the occurrence probabilities of the nine pieces of non-input information Evm, the apparatus may perform the processing in steps S7015 to S7022 three times.

The processing in steps S3030 to S3060 is the same as that in the first embodiment.

With the above processing, even if the database 300 stores no past case which has both the already input information Ef and the non-input information Evm, the apparatus can calculate the occurrence probability of non-input information by forming the second inference unit. In this case, even with respect to an unknown case which does not exist in the database, it is possible to estimate the occurrence probability of non-input information by using other data stored in the database. This technique is especially effective when the number of known cases stored in the database is small.

Third Embodiment

In the first embodiment, the apparatus selects, as presentation non-input information, non-input information for which an evaluation value W as the product of an occurrence probability and an influence degree is maximum. However, the method of selecting presentation non-input information is not limited to this, and it is possible to perform selection by using other methods. A medical diagnosis support apparatus according to the third embodiment selects presentation non-input information by processing different from that in the first embodiment.

Note that the arrangement of the medical diagnosis support apparatus according to this embodiment is the same as that shown in FIG. 1 in the first embodiment. However, the third embodiment differs from the first embodiment in that the occurrence probability of non-input information obtained by a non-input information probability calculation unit 106 is output to a non-input information obtaining unit 104. In addition, the processing executed by the non-input information obtaining unit 104 and a selection unit 112 differs from that in the first embodiment. The medical diagnosis support apparatus according to this embodiment will be described below with reference to only portions different from the first embodiment.

Figure 5:
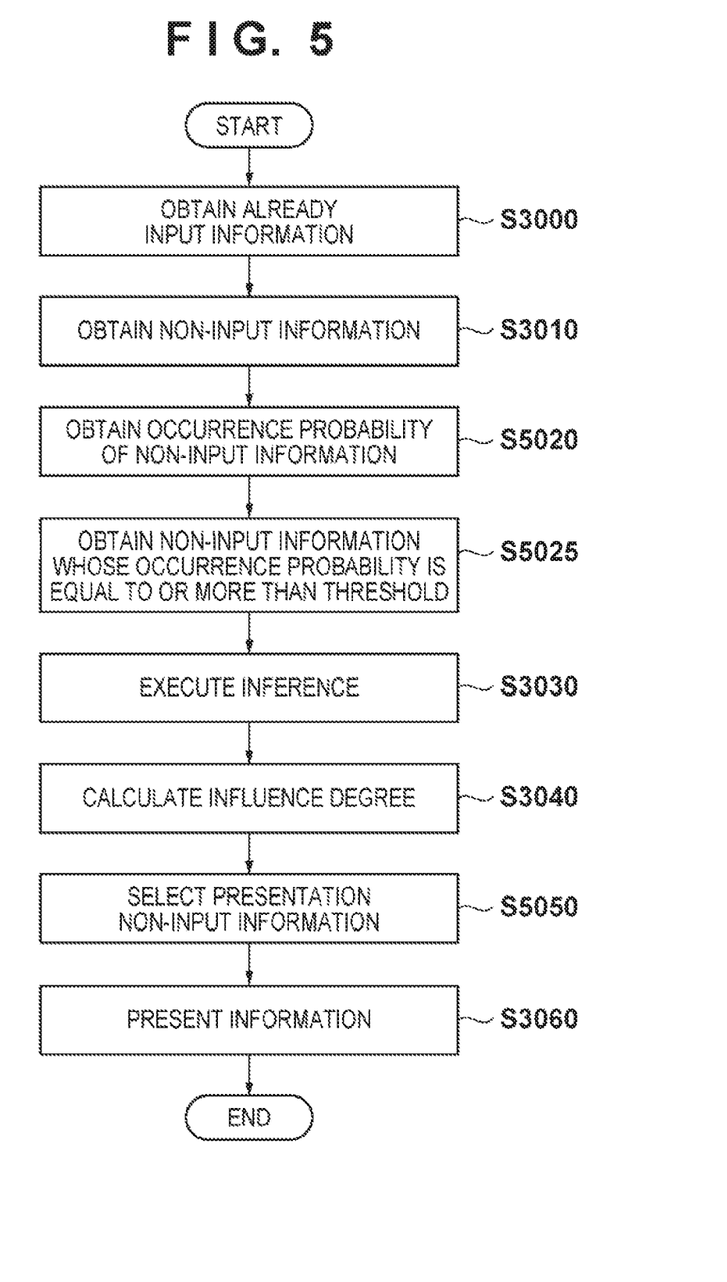
FIG. 5 is a flowchart showing a processing procedure for a medical diagnosis support method according to the third embodiment.

The basic arrangement of a computer which implements a medical diagnosis support apparatus 100 by executing software is the same as that shown in FIG. 2 in the first embodiment. FIG. 5 is a flowchart for explaining overall processing performed by the medical diagnosis support apparatus 100.

The processing in steps S3000 and S3010 is the same as that in the first embodiment. The non-input information obtained in step S3010 is output to only the non-input information probability calculation unit 106.

In step S5020, the non-input information probability calculation unit 106 of the medical diagnosis support apparatus 100 obtains the occurrence probability of each non-input information Evm by the same processing as that in the first embodiment. The obtained occurrence probability is output to the non-input information obtaining unit 104.

In step S5025, the medical diagnosis support apparatus 100 causes the non-input information obtaining unit 104 to select (choose) non-input information whose occurrence probability Pc(Evm) becomes equal to or more than a predetermined threshold. The selected non-input information is output to an inference unit 108 and the selection unit 112. This embodiment executes the following processing for only the non-input information (whose occurrence probability Pc(Evm) becomes equal to or more than a predetermined threshold) selected in step S5025.

The processing in steps S3030 and S3040 is the same as that in the first embodiment. Note however that non-input information as a processing target is limited to that selected in step S5025.

In step S5050, the medical diagnosis support apparatus 100 causes the selection unit 112 to select presentation non-input information based on the influence degree of each non-input information obtained in step S3040. More specifically, the apparatus selects, as presentation non-input information, Evm for which an influence degree IR(Evm) is maximum. In other words, the apparatus selects presentation non-input information which provides a maximum evaluation value W(Evm) as evaluation value W(Evm)=IR(Evm). Since the non-input information to be processed in this step is that selected in step S5025, the apparatus selects presentation non-input information based on the occurrence probability and influence degree of non-input information by the processing in steps S5020 to S5050.

The processing in step S3060 is the same as that in the first embodiment. The above processing implements the arrangement configured to select pieces of non-input information whose occurrence probabilities Pc(Evm) are equal to or more than a predetermined threshold and then select from them, as presentation non-input information, non-input information whose influence degree IE(Evm) is maximum. In this case, since non-input information whose occurrence probability is extremely low is excepted even if it exhibits a high influence degree, it is possible to perform selection with importance being attached to occurrence probability. In addition, since the apparatus executes the processing in steps S3030 and S3040 for only the non-input information selected in step S5025, it is possible to implement efficient processing.

(First Modification)

In each embodiment described above, the doctor interprets the medical images displayed by the medical diagnosis support apparatus 100 in step S3000 to obtain interpretation findings as already input information. However, the method of obtaining already input information and non-input information is not limited to this. For example, it is possible to use, as input information (already input information/non-input information), medical examination data including past interpretation reports and medical records associated with an object to be examined, other kinds of information which can be used for diagnosis support processing, and the like.

(Second Modification)

Figure 8:
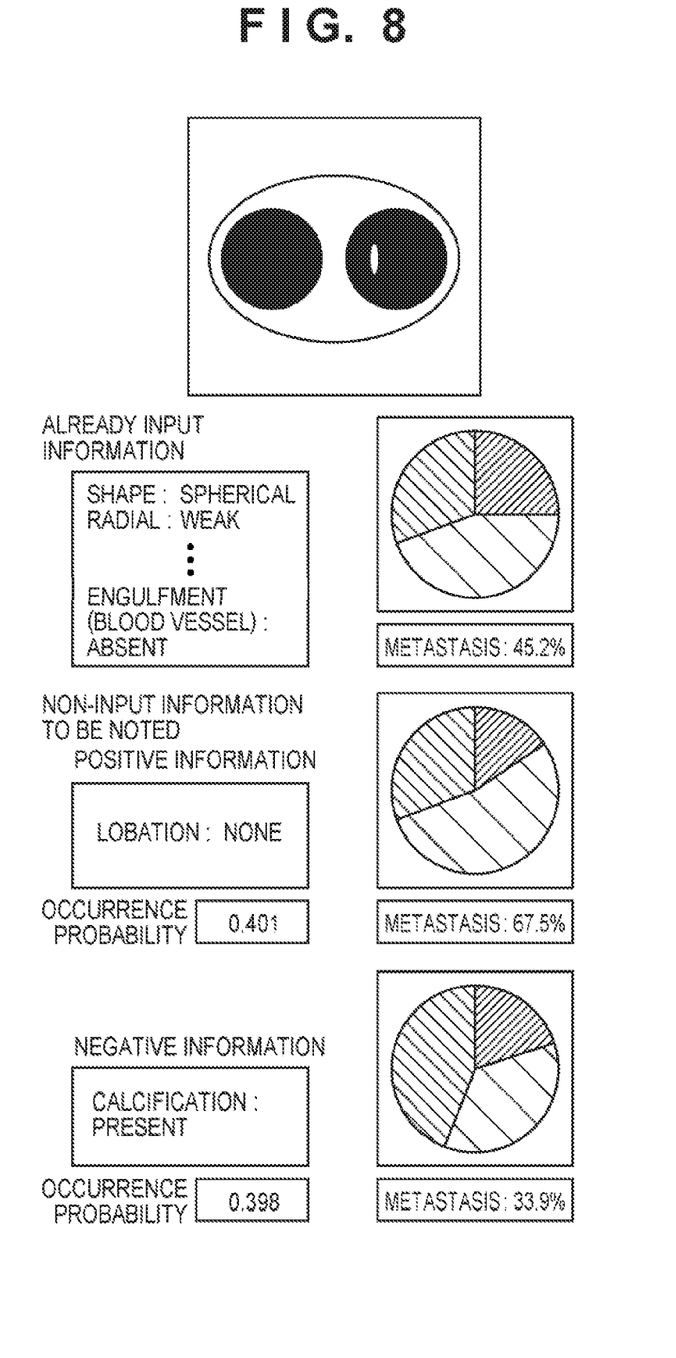
FIG. 8 is a view showing an example of presented information according to another embodiment.

In each embodiment described above, the apparatus obtains the influence degree of non-input information with respect to a diagnosis name exhibiting the maximum inference probability when already input information is input in step S3040. However, the influence degree of non-input information may be obtained for each diagnosis. The apparatus may select presentation non-input information which provides the maximum evaluation value W for each diagnosis name in steps S3050 and S5050 and present information associated with presentation non-input information selected for each diagnosis name in step S3060. This can present the user with non-input information which influences a diagnosis name other than diagnosis names obtained as already input information inference results. In the processing in step S3040, the apparatus may obtain an influence degree as a value with a position/negative sign without using any absolute value in equation (2). The apparatus may select, as presentation non-input information, each of pieces of non-input information respectively corresponding to the evaluation value W exhibiting the maximum positive value and the evaluation value W exhibiting the maximum negative value (absolute value) in steps S3050 and S5050 and present information associated with each presentation non-input information in step S3060. In the example shown in FIG. 8, the apparatus obtains and displays non-input information corresponding to the maximum positive value (Ev4 in FIG. 6) and non-input information corresponding to the maximum negative evaluation value (Ev5 in FIG. 6). This makes it possible to present the user with each of pieces of non-input information having a positive influence on an already input information inference result and having a negative influence on the already input information inference result.

(Third Modification)

In each embodiment described above, the apparatus selects one piece of non-input information as presentation non-input information in steps S3050 and S5050. However, the apparatus may select a plurality of pieces of non-input information as presentation non-input information. For example, the apparatus may select, as presentation non-input information, all pieces of non-input information corresponding to the evaluation values W which are equal to or more than a predetermined threshold. This makes it possible to present the user with all pieces of non-input information having great influences without omission.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a continuation of U.S. application Ser. No. 13/423,495, filed on Mar. 19, 2012, which claims the benefit of Japanese Patent Application No. 2011-070397, filed Mar. 28, 2011, and Japanese Patent Application No. 2012-014584, filed Jan. 26, 2012 which are hereby incorporated by reference herein in their entirety.

What is claimed is:

1. A medical diagnosis support apparatus which provides information for supporting medical diagnosis, comprising:
    an input obtaining unit that obtains at least one interpretation finding item as a piece of already input information for a target case, wherein the piece of already input information is input by a user;
    a non-input obtaining unit that obtains interpretation findings items which have not been input for the target case as pieces of non-input information, by using the already input information and referring to a database;
    an occurrence probability obtaining unit that obtains an occurrence probability of the piece of non-input information based on a co-occurrence frequency between the already input information and non-input information, wherein the occurrence probability depends on the co-occurrence frequency;
    a result obtaining unit that obtains a first inference result based on the piece of already input information, and obtain a second inference result based on the piece of already input information and the piece of non-input information, second inference results being obtained for the pieces of non-input information;
    an influence degree calculation unit that calculates an inference-influence degree for the pieces of non-input information based on the first inference result and the second inference result, inference-influence degrees obtained for the pieces of non-input information; and
    a selection unit that selects a non-input information to be presented from the piece of non-input information based on the inference-influence degree and the occurrence probability corresponding to the piece of non-input information.

2. The apparatus according to claim 1, wherein the selection unit selects the piece of non-input information based on an evaluation value which depends on the occurrence probability and the inference-influence degree.

3. The apparatus according to claim 2, wherein the selection unit selects the piece of non-input information corresponding to the evaluation value which is maximum among the evaluation values.

4. The apparatus according to claim 1, wherein the selection unit selects the piece of non-input information corresponding to the calculated inference-influence degree which is positive and maximum in absolute value and the piece of non-input information corresponding to the calculated inference-influence degree which is negative and maximum in absolute value.

5. The apparatus according to claim 1, wherein the occurrence probability is a probability at which each piece of non-input information is input for a diagnosis target based on a past diagnosis result at least partly including already input information about the diagnosis target.

6. The apparatus according to claim 1, wherein the influence degree calculation unit calculates the inference-influence degree of the piece of non-input information corresponding to the occurrence probability which is not less than a threshold.

7. The apparatus according to claim 1, further comprising a presentation unit that presents the piece of non-input information selected by the selection unit.

8. The apparatus according to claim 7, the presentation unit presents an image of a target diagnosis, the first inference result and the selected non-input information side by side.

9. A medical diagnosis support apparatus which provides information for supporting medical diagnosis, comprising:
an input obtaining unit that obtains at least one interpretation finding item as a piece of already input information for a target case, wherein the piece of already input information is input by a user;
a non-input obtaining unit that obtains interpretation findings items which have not been input for the target case as pieces of non-input information, by using the already input information and referring to a database;
an occurrence probability obtaining unit that obtains an occurrence probability of at least one of the piece of non-input information inferred based on a case stored in a database and the piece of non-input information which can be input;
a result obtaining unit that obtains a first inference result based on the piece of already input information, and obtain a second inference result based on the piece of already input information and the piece of non-input information, second inference results being obtained for the pieces of non-input information;
an influence degree calculation unit that calculates an inference-influence degree for the pieces of non-input information based on the first inference result and the second inference result, inference-influence degrees obtained for the pieces of non-input information; and
a selection unit that selects a non-input information to be presented from the piece of non-input information based on the inference-influence degree and the occurrence probability corresponding to the piece of non-input information.

10. A medical diagnosis support method which provides information for supporting medical diagnosis, comprising:
an input obtaining step of obtaining at least one interpretation finding item as a piece of already input information for a target case, wherein the piece of already input information is input by a user;
a non-input obtaining step of obtaining interpretation findings items which have not been input for the target case as pieces of non-input information, by using the already input information and referring to a database;
an occurrence probability obtaining step of obtaining an occurrence probability of the piece of non-input information based on a co-occurrence frequency between the already input information and non-input information, wherein the occurrence probability depends on the co-occurrence frequency;
a result obtaining step of obtaining a first inference result based on the piece of already input information, and obtain a second inference result based on the piece of already input information and the piece of non-input information, second inference results being obtained for the pieces of non-input information;
an influence degree calculation step of calculating an inference-influence degree for the pieces of non-input information based on the first inference result and the second inference result, inference-influence degrees obtained for the pieces of non-input information; and
a selection step of selecting a non-input information to be presented from the piece of non-input information based on the inference-influence degree and the occurrence probability corresponding to the piece of non-input information.

11. A medical diagnosis support system which provides information for supporting medical diagnosis, comprising:
an input obtaining unit that obtains at least one interpretation finding item as a piece of already input information for a target case, wherein the piece of already input information is input by a user;
a non-input obtaining unit that obtains interpretation findings items which have not been input for the target case as pieces of non-input information, by using the already input information and referring to a database;
an occurrence probability obtaining unit that obtains an occurrence probability of the piece of non-input information based on a co-occurrence frequency between the already input information and non-input information, wherein the occurrence probability depends on the co-occurrence frequency;
a result obtaining unit that obtains a first inference result based on the piece of already input information, and obtain a second inference result based on the piece of already input information and the piece of non-input information, second inference results being obtained for the pieces of non-input information;
an influence degree calculation unit that calculates an inference-influence degree for the pieces of non-input information based on the first inference result and the second inference result, inference-influence degrees obtained for the pieces of non-input information; and
a selection unit that selects a non-input information to be presented from the piece of non-input information based on the inference-influence degree and the occurrence probability corresponding to the piece of non-input information.

* * * * *